United States Patent [19]

Dotzlaf et al.

[11] Patent Number: 5,082,772
[45] Date of Patent: Jan. 21, 1992

[54] PROCESS FOR PREPARING DEACETYLCEPHALOSPORIN C

[75] Inventors: Joe E. Dotzlaf; Wu-Kuang Yeh, both of Greenwood, Ind.

[73] Assignee: Eli Lilly and Company, Indianapolis, Ind.

[21] Appl. No.: 261,437

[22] Filed: Oct. 24, 1988

[51] Int. Cl.$^5$ ............... C12P 35/06; C12N 9/02; C12N 9/86/1/00
[52] U.S. Cl. ................... 435/49; 435/189; 435/231; 435/886; 424/94.6
[58] Field of Search ............... 424/94.6; 435/231, 886, 435/189, 49

[56] References Cited

U.S. PATENT DOCUMENTS

| | | | |
|---|---|---|---|
| 3,847,742 | 11/1974 | Higgens et al. | 435/49 |
| 4,510,246 | 4/1985 | Wolfe et al. | 435/183 |
| 4,536,476 | 8/1985 | Wolfe et al. | 435/183 |
| 4,693,977 | 9/1987 | Wolfe et al. | 435/180 |

FOREIGN PATENT DOCUMENTS

| | | | |
|---|---|---|---|
| 0044736 | 1/1982 | European Pat. Off. | 435/49 |
| 0233715 | 8/1987 | European Pat. Off. | |
| 55-39735 | 3/1980 | Japan | 435/49 |

OTHER PUBLICATIONS

Demain et al., *Microbial Degradation of Cephalosporin C*, Nature, pp. 909 and 910, 1963.
Rollins et al., *Purification and Initial Characterization*, Canadian Journal of Micro., vol. 34, No. 11, pp. 1196–1202.
Dotzlaf, J. E., and Yeh, W-K., "Copurification and Characterization of Deacetoxycephalosporin C Synthase/Hydroxylase . . .", *J. Bacteriol.*, Apr. 1987, pp. 1611–1618.
Jensen, S. E. et al., "Deacetoxycephalosporin C Synthetase and Desacetoxycephalosporin C Hydroxylase are Two Separate Enzymes in S. clavuligerus", *J. Antibiotics* 38, 263–265, 1985.
Cortes, J., et al., *J. Gen. Microbiol.* (1987), 133, 3165–3174.

*Primary Examiner*—Douglas W. Robinson
*Assistant Examiner*—Michael V. Meller
*Attorney, Agent, or Firm*—William B. Scasnlon; Leroy Whitaker

[57] ABSTRACT

Deacetoxycephalosporin C synthase obtained from cell-free extracts of *Streptomyces clavuligerus* was purified to near homogeneity and characterized in inactive form. The amino acid sequence was determined and the synthase recombinantly reproduced in active form in *E. coli*. The recombinantly produced synthase is provided in about 97% pure form by a chromatographic process. The synthase lacks DAOC hydroxylase function; however, it possesses the ability to transform 3-exomethylenocephalosporin C to deacetylcephalosporin C.

5 Claims, 5 Drawing Sheets

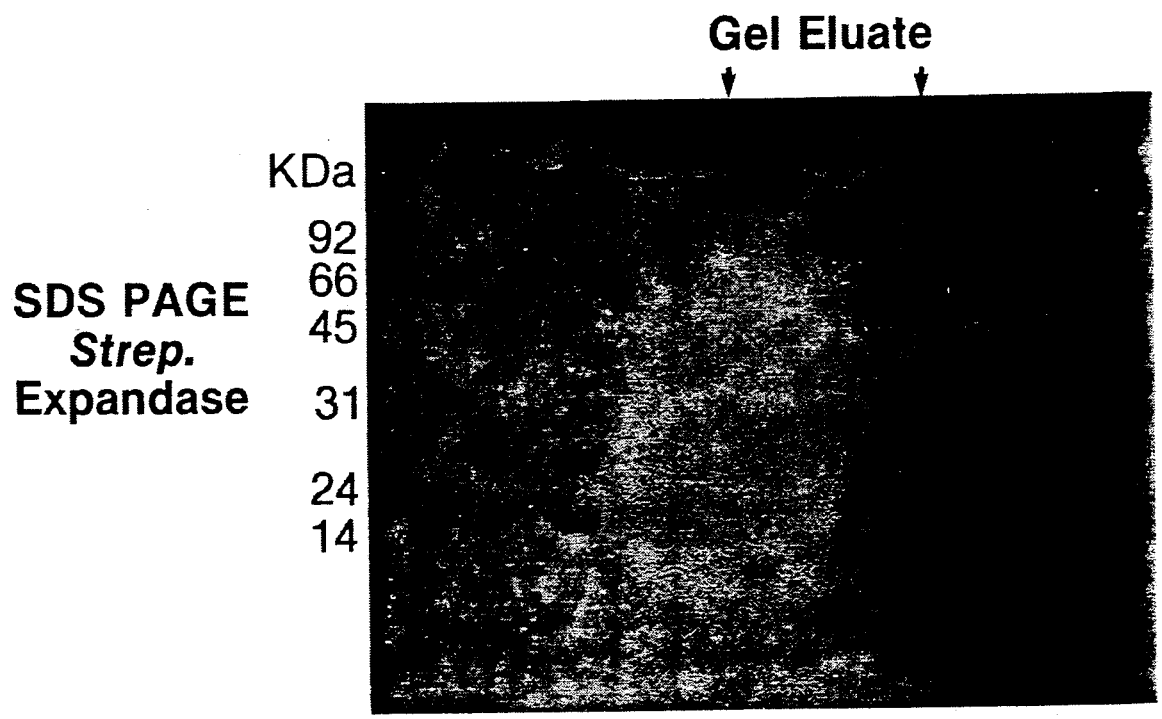

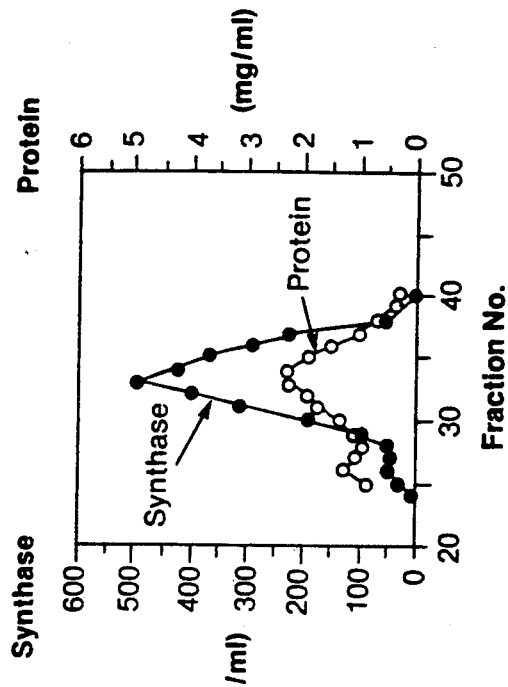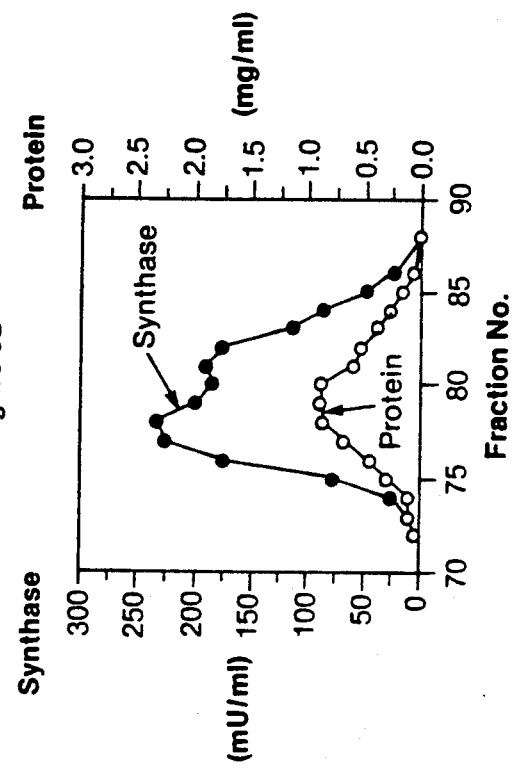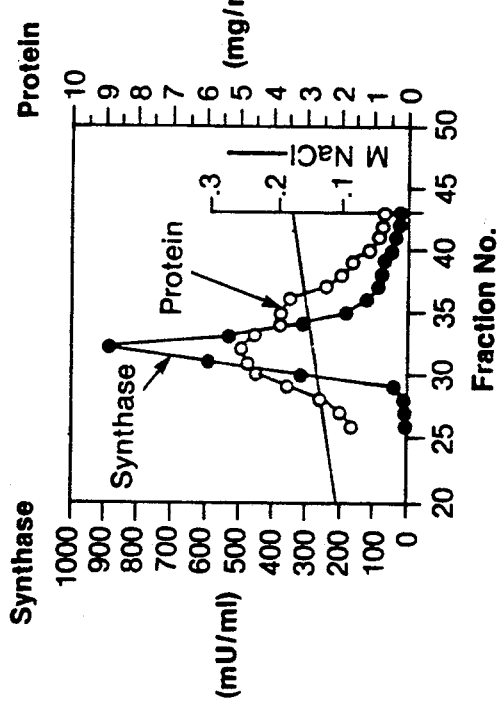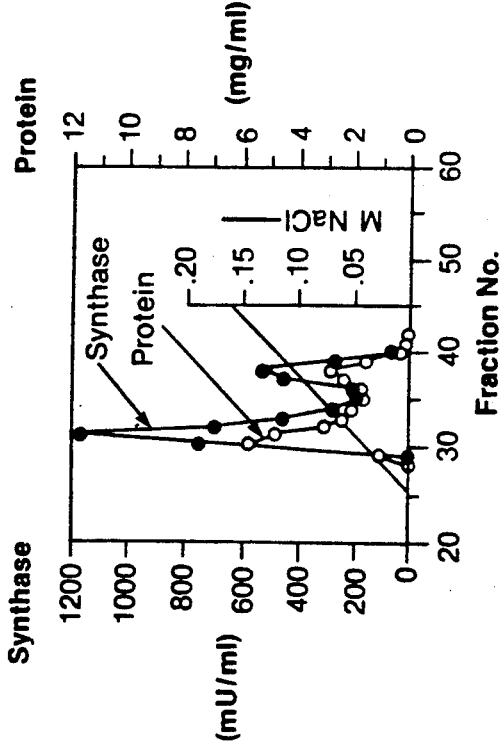

PROCESS FOR PREPARING DEACETYLCEPHALOSPORIN C

BACKGROUND OF THE INVENTION

This invention relates to enzyme technology. In particular, it relates to the enzyme deacetoxycephalosporin C (DAOC) synthase, also known as "expandase", obtained from *Streptomyces clavuligerus*.

The enzyme expandase mediates ring expansion of penicillin N to DAOC during the biosynthesis of cephalosporin C. DAOC is then converted to deacetylcephalosporin C (DAC) by the enzyme hydroxylase and the latter to cephalosporin C via action of an acetyl transferase.

The bifunctional enzyme, expandase/hydroxylase, obtained from cell-free extracts of *Cephalosporium acremonium* is described by U.S. Pat. No. 4,753,881. The expandase enzyme obtained from *S. clavuligerus* provided herein differs from that obtained from *C. acremonium* in that inter alia it lacks the hydroxylase activity for converting DAOC to DAC.

Because of the importance of the cephalosporin antibiotics in the treatment of infectious disease, the availability of expandase in purified form enables one to study the development of industrial processes for producing these antibiotics. Further, the availability of the enzyme permits one to study the effect of the enzyme on modified substrates which could lead to structurally different antibiotics.

Brief Description of the Drawings

FIG. 2 shows the SDS-PAGE of *S. clavuligerus* DAOC synthase protein.

FIG. 3 shows the purification of recombinant *E. coli* DAOC synthase. A. DEAE-Sepharose chromatography; B. Gel-filtration; C. MONO Q chromatography;.D. Superose FPLC.

DETAILED DESCRIPTION

Figure 1:
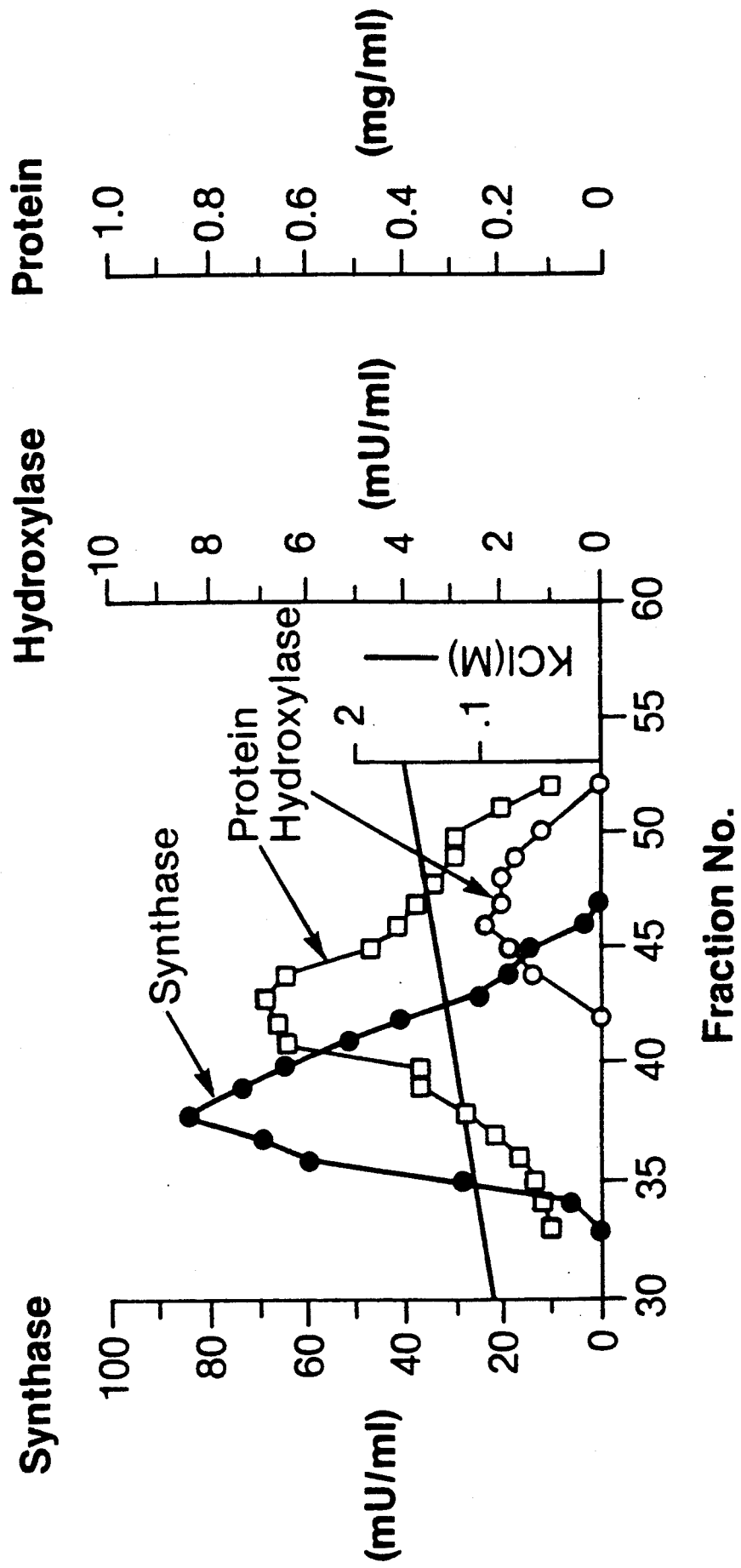
FIG. 1 shows the chromatographic separation of native DAOC synthase from DAOC hydroxylase on DEAE-Trisacryl.

The purified deacetoxycephalosporin C synthase provided by this invention is obtained from *Streptomyces clavuligerus* and exhibits expandase activity providing deacetoxycephalosporin C with the substrate penicillin N. In contrast to the bifunctional expandase/hydroxylase enzyme obtained from *Cephalosporium acremonium*, the purified enzyme of this invention lacks the hydroxylase activity for converting DAOC to desacetylcephalosporin C (DAC). However, the *S. clavuligerus* derived enzyme, in its partially purified state, catalyzes the hydroxylation of 3-exomethylenecephalosporin C to DAC.

The enzyme has been isolated from cell-free extracts of *S. clavuligerus* and purified in inactive form by chromatography. The amino-terminal sequence of the enzyme was determined and used in cloning of the expandase gene into *Escherichia coli*, J. R. Miller et al., copending application serial No. 192,273, filed May 9, 1988. The enzyme can be recovered in greater abundance from cultures of the recombinant E. coli and purified to apparent homogeneity in active form by a five-step chromatographic procedure. The recombinantly produced enzyme has been shown to be identical with the native enzyme.

The purified native enzyme obtained from cell-free extracts of *S. clavuligerus* can be partially stabilized by phenylmethylsulfonyl fluoride and ethanol. Thus stabilized, the enzyme exhibits an increase in half-life from 20 h to 48 h and can be purified by a three-step chromatographic procedure followed by gel-electrophoretic elution.

The enzyme is a protein monomer which has a molecular weight of 34,600 daltons as derived from the nucleotide sequence; 34,000 to 35,000 by SDS-PAGE. The amino-terminal residue of the enzyme is free (unblocked). The 22-amino acid sequence of the aminoterminal residue of the native enzyme has been determined by conventional means and is as follows: Met-Asp-Thr-Thr-Val-Pro-Thr-Phe-Ser-Leu-Ala-Glu-Leu-Gln-Gln-Gly-Leu-His-Gln-Asp-Glu-Phe. The data obtained for the amino-terminal residue of the 22-amino acid sequence of the recombinantly produced enzyme show a difference in the fourth amino acid. In the recombinant enzyme, the fourth amino acid appears to be isoleucine (Ile) while, as shown above, for the native enzyme threonine (Thr) is the fourth amino acid. Otherwise, the sequences are identical. Whether this difference is related to multiple isoenzymes or to an experimental error is uncertain at present.

The amino acid composition of the purified enzyme is shown in Table 1 below.

TABLE 1

| Amino Acid Composition of Expandase | |
|---|---|
| Amino Acid | No. of Residues per 34,600 Dalton |
| Asp + Asn | 28 |
| Thr | 25[a] |
| Ser | 24[a] |
| Glu + Gln | 33 |
| Pro | 18 |
| Gly | 25 |
| Ala | 27 |
| Cys | 6[b] |
| Val | 20 |
| Met | 5 |
| Ile | 10 |
| Leu | 25 |
| Tyr | 10 |
| Phe | 20 |
| His | 8 |
| Lys | 7 |
| Arg | 23 |
| Trp | 2[c] |

[a]Determined by extrapolation to zero time of hydrolysis
[b]Determined as cysteic acid
[c]Determined by hydrolysis in the presence of thioglycolic acid The purified enzyme exhibits two distinct isoelectric points: 5.3±0.2 and 6.1±0.2.

The purified enzyme exhibits its optimal synthase activity with 0.2 to 15 mU of enzyme in 50 mM HEPES Buffer, pH 7, in the presence of 100 mM α-ketoglutarate, 50 μM ferrous ion, and 500 μM DTT in the conversion of 100 μM penicillin N to DAOC over a 15 min. reaction time at 36° C.

The enzyme exhibits a narrow substrate specificity. No synthase activity was observed for the enzyme (HPLC detectable) with isopenicillin N, penicillin G, penicillin V, ampicillin or 6-aminopenicillanic acid under the above-noted optimum conditions for converting penicillin N to DAOC.

The enzyme requires α-ketoglutarate, ferrous ion and oxygen for expression of its catalytic activity. The DAOC synthase activity is stimulated by dithiothreitol (DTT). No detectable stimulation by ATP was observed.

The requirement of ferrous ion for expression of enzyme activity could not be replaced by magnesium, manganous, cobaltous, calcium, cuprous, nickel, zinc, sodium or potassium ions. Ferric ion can substitute for ferrous ion when in the presence of DTT and ascorbate, although the enzyme was slightly less active. The enzyme activity is inhibited by $Zn^{2+} > Co^{2+} > Ni^{2+}$ in the order indicated.

The enzyme is highly sensitive to inhibition of its DAOC synthase activity by EDTA (ethylenediamine tetraacetic acid) and 1,10-phenanthroline. The enzyme was also highly susceptible to inhibition by certain sulfhydryl reagents, e.g., p-hydroxymercuribenzoate (p-HMB), 5,5'-dithiobis-2-nitrobenzoic acid (DTNB) and N-ethylmaleimide (NEM), and was slightly inhibited by iodoacetic acid. Following complete inactivation by 0.2 mM DTNB in 0.5 min at 4° C., the enzyme's synthase activity is fully restored in 30 min by addition of 2 mM DTT to the reaction mixture.

The following Table 2 shows the effect on the enzyme of the metal chelators and sulfhydryl reagents discussed above.

TABLE 2

Effect of Metal Chelators and Sulfhydryl Reagents on DAOC Synthase[1]

| Additive | Concentration (mM) | Relative Activity (%) |
|---|---|---|
| None | — | 100 |
| o-Phenanthroline | 0.02 | 63 |
|  | 0.2 | 0 |
| EDTA | 0.02 | 65 |
|  | 0.2 | 0 |
| p-HMB | 0.1 | 0 |
|  | 1.0 | 0 |
| DTNB | 0.1 | 70 |
|  | 1.0 | 0 |
| NEM | 0.1 | 55 |
|  | 1.0 | 0 |
| Iodoacetic acid | 0.1 | 100 |
|  | 1.0 | 65 |

[1]Enzymatic reactions were conducted in the presence of 0.06 mN $FeSO_4$ and 0.1 mM DTT. The enzyme was incubated with the indicated inhibitor for 1 min prior to the initiation of the reaction with penicillin N.

Figure 5:
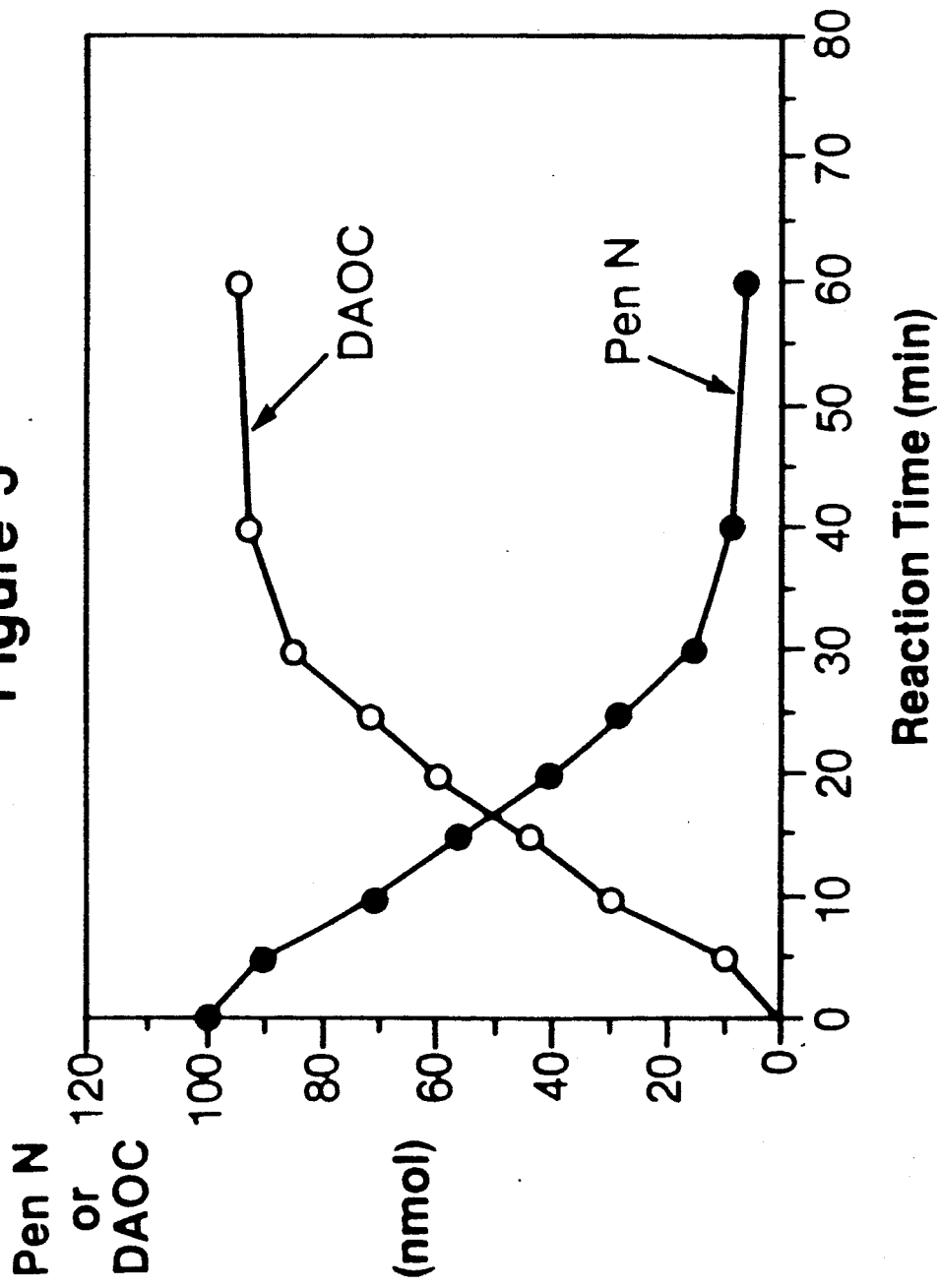
FIG. 5 shows the stoichiometric analysis of recombinant DAOC synthase catalyzed conversion of penicillin N.

In the conversion of penicillin N to DAOC by the purified synthase provided herein, the molar ratio for DAOC formation/penicillin N disappearance over 60 min of the reaction remained in the range of 0.90–0.98 as shown in FIG. 5. The conversion of penicillin N to DAOC was 94% complete under the reaction conditions.

The purified synthase provided by the invention exhibits optimal catalysis in the conversion of penicillin N to DAOC in the presence of ferrous ion, α-ketoglutarate and oxygen at 36° C. in either 50 mM Tris-HCl buffer, pH 7.4, or HEPES buffer [N-(2-hydroxyethyl)-piperazine-N'-2-ethanesulfonic acid], pH 7.0.

The kinetics of the native enzyme and recombinant enzyme were determined under the optimal reaction conditions for the enzyme, i.e., at pH 7.0 in 50 mM HEPES buffer at 36° C. The $K_m$ of the recombinantly produced DAOC synthase for penicillin N was 29 μM and for α-ketoglutarate was 18 μM as determined by the Lineweaver-Burk method. The $K_a$ of the enzyme for $Fe^{2+}$ was similarly determined as 8 μM. The $V_{max}$ of the recombinant synthase was 0.432 μmol DAOC formed/min/mg protein.

The corresponding kinetic constants for the native synthase, evaluated with the partially purified enzyme (Table 3, Mono Q eluate) under the same optimal reaction conditions, except that HEPES buffer was replaced with Tris-HCl buffer, were $K_m$ (penicillin N) = 35 μM, (α-ketoglutarate) = 22 μM, and $K_a$ ($Fe^{2+}$) = 4 μM.

As noted hereinabove, the purified synthase of the invention lacks the hydroxylase activity for converting DAOC to DAC (deacetylcephalosporin C) but possesses the ability to convert 3-exomethylenecephalosporin C to DAC. Accordingly, this invention provides a process for converting 7β-(α-aminoadipamido)-3-exomethylenecepham-4-carboxylic acid "3-exomethylenecephalosporin C" represented by the formula

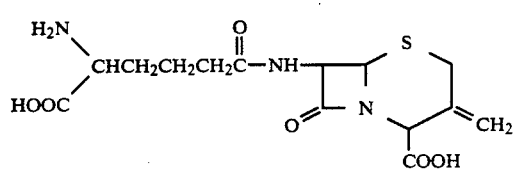

to deacetylcephalosporin C which comprises mixing 3-exomethylenecephalosporin C at a temperature between about 30° C. and about 40° C. in an aqueous medium containing ferrous ion, α-ketoglutarate and oxygen at a pH between about 6.8 and about 7.6 with Streptomyces clavuligerus derived synthase.

The process is carried out in the desired pH range in the presence of a buffer such as Tris-HCl buffer. Preferably, the pH of the mixture is maintained at about pH 7.0 to about 7.4. The process is preferably carried out at a temperature of about 36° C. at which temperature the purified synthase appears to show its best activity Ferrous ion is present preferably at a concentration between about 20 μM and about 100 μM and α-ketoglutarate at a concentration between about 20 μM and about 300 μM.

Oxygen can be provided from the atmosphere in sufficient amount when the process is carried out on a small scale such as in a small laboratory-size beaker or flask; however, for larger scale reactions, oxygen can be bubbled into the reaction mixture.

As with most enzymatic reactions when carried out batchwise, the reaction mixture is provided with good agitation by stirring or shaking. Alternatively, the process can be carried out with immobilized synthase wherein the aqueous medium containing the 3-exomethylenecephalosporin C, ferrous ion, α-ketoglutarate, and buffered as described above, is brought into contact with the immobilized enzyme on an insoluble support. Such supports are well known, e.g., a cross-linked divinylbenzene resin or a polyacrylicmethacrylic resin and may be in the form of beads of various sizes and pore dimensions. The immobilized enzyme may be packed into a suitable column and the aqueous medium containing the 3-exomethylenecephalosporin C passed through the column. Oxygen may be passed up the column or may be admitted in some other manner, e.g., it may be passed into the aqueous medium as it enters the column.

Generally, an excess of the purified synthase is used in the process. In addition to $Fe^{2+}$, α-ketoglutarate and oxygen which are necessary for expression of enzymatic activity, other factors such as reducing agents, e.g., dithiothreitol, β-mercaptoethanol, dithioerythreitol and ascorbic acid may have a beneficial effect on either the yield or the rate of the process.

The 3-exomethylenecephalosporin C is a strong inhibitor of the DAOC synthase activity of the enzyme and the 3-exomethylenecephalosporin C hydroxylase activity of the enzyme will not convert DAOC to DAC. Accordingly, it appears that the 3-exo-hydroxylase activity is a distinct function of the enzyme.

The purified expandase provided herein can be obtained from cell-free extracts of Streptomyces clavuligerus by the purification process of this invention. S. clavuligerus has been available for some time and has been employed by numerous researchers in the study of cephalosporin biosynthesis, e.g., Jensen, S. E., et al., J. Antibiotics, 38, 263, 1985; Wolfe, S., et al., Science, Vol. 226, 1386–1392, 1984; and U.S. Pat. No. 4,536,476. S. clavuligerus is also available from the American Type Culture Collection under the deposit number ATCC 27064.

According to the process, cell-free extracts of S. clavuligerus are prepared and stabilized during preparation from whole cells at pH 7.5 with a protease inhibitor such as phenylmethylsulfonyl fluoride and ethanol at a temperature of about 0° C. to about 4° C. Centrifugation of the stabilized extract provides a cell-free stabilized crude extract. The crude extract is first chromatographed at a temperature between about 0° C. and about 4° C. over a weak anionic resin with the DAOC synthase eluting with a KCl linear gradient as a single activity peak well separated from DAOC hydroxylase activity. The DAOC synthase peak fractions are pooled and concentrated by ultrafiltration and the concentrate subjected to gel filtration. A single peak of activity is eluted with Tris-HCl, pH 7.5, buffer containing 10% ethanol. The peak fractions containing 60% of the activity are pooled and subjected to Fast Protein Liquid Chromatography (FPLC) over a strong anionic resin and the synthase eluted with a linear gradient of KCl in buffer. A single activity peak is obtained.

The main protein (Mr of 34,000) from a portion of the fraction with the highest activity can be purified to near homogeneity by electrophoretic elution from an SDS-PAGE gel.

The purification process can be considered as a three-step process comprising 1) the chromatography over a weak anionic resin which separates DAOC hydroxylase activity, 2) gel filtration, and 3) FPLC chromatography over a strong anionic resin.

The steps of the process are carried out at a temperature of about 0° C. to about 4° C. Initially, a crude cell-free extract is prepared with harvested whole cells of Streptomyces clavuligerus. The cells are suspended in 15 mM Tris-HCl, pH 7.5, buffer containing 10% ethanol by volume, hereinafter referred to as E buffer. The cells are broken up by sonication during which a protease inhibitor such as phenylmethylsulfonyl fluoride or diisopropyl fluorophosphate is present. The sonicated mixture is centrifuged at 40,000 ×g for about 30 min. The supernatant is used as the crude enzyme extract.

In the first step of the process, the cold crude extract is chromatographed over a weak anionic resin previously equilibrated with E buffer. Weak anionic resins which can be used are the cellulose derivatives, for example, diethylaminoethyl cellulose such as the commercially available DEAE cellulose, Whatman, Inc., and the acrylic copolymer resins such as copolymers of N-[tris-(hydroxymethyl)methyl]acrylamide with a secondary monomer of an anionic acrylic derivative. The commercially available diethylaminoethyl trisacryl such as DEAE-Trisacryl LS, IBF Biotechnics, Inc., is a suitable anionic resin.

The cold crude extract is applied to the column, the column washed with E buffer and the bound protein is eluted with a linear gradient of potassium chloride (0–0.35 M) in E buffer system. DAOC synthase is eluted as a single activity peak well separated from the DAOC hydroxylase activity peak as shown in FIG. 1 of the drawings.

The peak fractions containing about 60% of the total synthase activity are pooled and concentrated to a small volume by ultrafiltration. The synthase concentrate is subjected to gel filtration in the second step of the process. The gel is equilibrated with E buffer prior to use and the protein is eluted from the gel with E buffer. In a typical filtration the synthase activity is obtained as a single peak. Gels of the cross-linked polysaccharide type are suitable for use in the process, for example, the cross-linked dextrans and agarose gels available commercially such as Sephadex, Sepharose and Superose (Pharmacia, Inc.) and Ultragel A44 (IBF Biotechnics, Inc., Villeneuve-la-Giaremere, France).

The peak fractions of the gel filtration containing about 60% of the total synthase activity are pooled and chromatographed by FPLC over a strong anionic exchange resin equilibrated with E buffer prior to use. A preferred resin is the polymeric anionic exchange resin Mono Q (Pharmacia, Inc.). The bound protein is eluted with a linear gradient of KCl (0–0.5 M) in E buffer. A single synthase activity peak was observed. The fraction with the highest activity was used to determine the characteristics of the purified enzyme described hereinabove.

The fractions from the single peak containing the synthase activity can be stored at −70° C. until needed.

As was mentioned hereinabove, the S. clavuligerus derived synthase has been recombinantly produced as described by J. R. Miller, et al., Ser. No. 192,273, filed May 9, 1988. The recombinantly produced synthase has also been purified and the enzyme found to be identical to the enzyme from the natural source.

This invention further provides a process for the recovery and purification of the recombinantly produced synthase.

The process for purifying the recombinant produced enzyme is similar to that described above for the purification of the native enzyme. However, because the recombinant enzyme is produced in more concentrated form and in greater abundance than from the natural source and because different alien proteins are produced by the two sources, the processes are distinct.

The enzyme produced by recombinant E. coli is concentrated in granules within the cells. In general, the process is carried out as follows. A granular extract of the enzyme is first chromatographed over a weak anionic exchange resin using a linear gradient of sodium chloride for elution. A single activity peak is obtained and the eluate fractions containing about 60% of the total enzyme activity are pooled. The volume of the pooled fraction is reduced to a small volume by ultrafiltration. The concentrate is subjected to gel filtration and the bound protein eluted from the gel with buffer to produce a single activity peak. The peak fractions containing about 60% of the total enzyme activity are pooled and supplemented with 0.1 mM penicillin N.

The combined fractions are then chromatographed (FPLC) over a strong anionic exchange resin with pH 8 buffer and the bound protein is eluted with a linear gradient of NaCl in pH 8 buffer. Two activity peaks are observed on assay. The fractions containing about 60% of the enzyme activity from the major peak are pooled and concentrated via ultrafiltration. The concentrate is subjected to gel filtration and the bound protein eluted with 0.1 M KCl supplemented buffer to produce two partially separated activity peaks. The fractions containing about 80% of the enzyme activity from the major peak are pooled and are subjected to FPLC over a strong anionic exchange resin with buffer, pH 7, supplemented with 0.05 M KCl. The column is eluted with a linear gradient of KCl in pH 7 buffer. The fractions of the main activity peak having a synthase activity of at least 275 mU/ml are combined and maintained at −70° C. for future use.

Initially, the synthase containing granules are isolated from the *E. coli* cells by homogenization of the cells in a buffered medium, e.g., 50 mM Tris-HCl, pH 7.5, buffer. The granules enriched in DAOC synthase can be separated by differential centrifugation at 8,000 ×g for about one minute. The granules are resuspended in buffer and solubilized with 5 M urea in 15 mM Tris-HCl, pH 8.0, containing 5 mM DTT and 10% by volume of glycerol (hereinafter UDG buffer). The mixture is centrifuged at 40,000 ×g for about 15 min. The supernatant granular extract containing crude DAOC synthase is then purified in the process provided herein.

The following process is carried out at a temperature between about 0° C. and about 4° C. All buffers are thoroughly degassed prior to use.

The crude extract is first chromatographed over a weak anion exchange resin such as one of those described hereinabove for use in the process for purifying the enzyme from the natural source. A preferred resin is DEAE-Sepharose (Pharmacia, Inc., Piscataway, NJ). The resin is first equilibrated with UDG buffer and, after loading the resin with crude extract, the resin is washed with UDG buffer. The bound protein is eluted with a linear salt gradient, e.g., KCl or NaCl, preferably NaCl (0–0.3 M). The synthase is observed as a single activity peak as shown in FIG. 3A of the drawings. The fractions containing about 60% of the total enzyme activity are pooled and concentrated to a small volume by ultrafiltration.

The concentrate is subjected to gel filtration over a suitable gel, preferably one such as Bio-Gel A0.5m available from Bio-Rad Laboratories, Richmond, CA. The gel is equilibrated with UDG buffer prior to use. The protein is eluted from the gel with UDG buffer, affording a single activity peak such as shown in FIG. 3B of the drawings.

Again the peak fractions containing about 60% of the total enzyme activity are pooled and supplemented with 0.1 mM penicillin N to stabilize the enzyme. The pool is subjected to FPLC over a strong anionic resin. Strong anionic resins such as those commercially available, e.g., Accell (Waters Associates), the QAE Sephadex (Pharmacia, Inc.) and Mono Q (Pharmacia, Inc.) can be used. A preferred resin is Mono Q. The resin is equilibrated with glycerolfree UDG buffer at pH 8.0 prior to use. The bound 5 proteins are eluted with a linear gradient of NaCl (0–0.5 M) in the equilibration buffer. Two activity peaks (major and minor) are obtained in the chromatography such as shown by FIG. 3C of the drawings.

The fractions containing about 60% of the enzyme activity from the major peak are combined and concentrated to a small volume by ultrafiltration. The concentrate is subjected to gel filtration over a suitable gel. A preferred gel is Superose (Pharmacia, Inc.) available commercially. The gel is equilibrated with the glycerol-free buffer prior to use and the protein is eluted with the glycerol-free buffer supplemented with 0.1 M KCl. Two partially separated activity peaks are observed such as shown in FIG. 3D of the drawings.

Figure 4A:
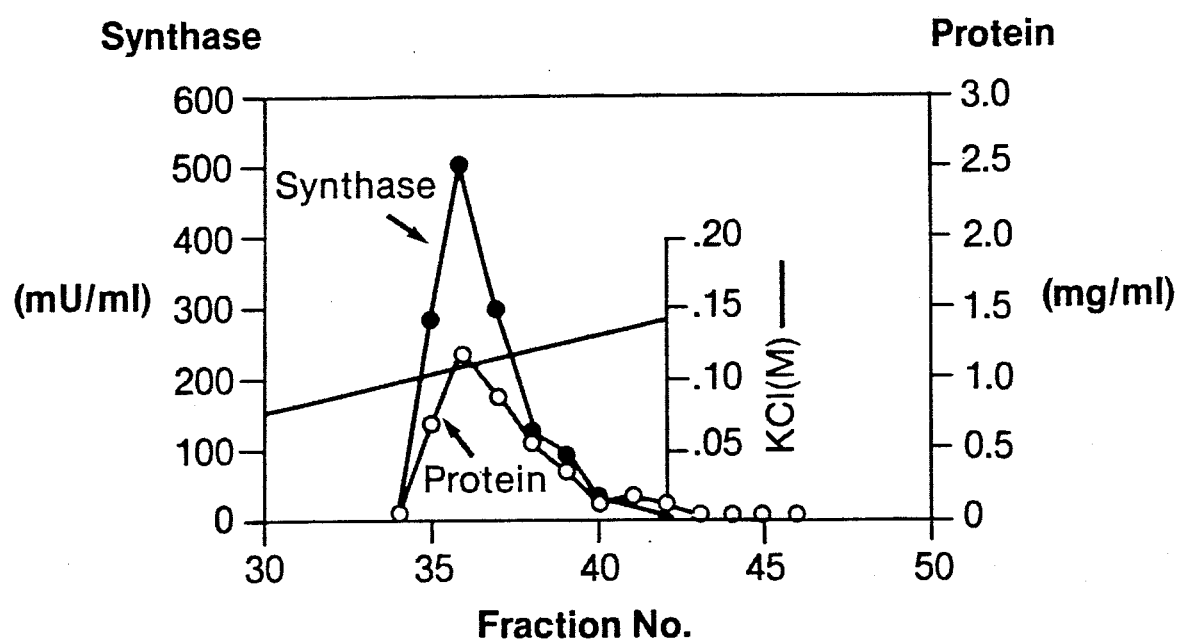
FIG. 4A shows the second Mono Q chromatography in the purification of recombinant synthase

Next the fractions containing about 80% of the enzyme activity from the major peak are pooled, supplemented with 0.1 mM penicillin N for stabilization and again chromatographed (FPLC) over a strong anion exchange resin such as Mono Q. The resin is equilibrated with the glycerol-free buffer at pH 7.0, rather than at pH 8.0 as with the UDG buffer of the first FPLC above described. The bound proteins are eluted with a linear gradient of KCl (0.05–0.2 M) contained in the equilibration buffer. The plot of the chromatogram shows the major synthase activity peak as shown in FIG. 4A of the drawings.

Figure 4B:
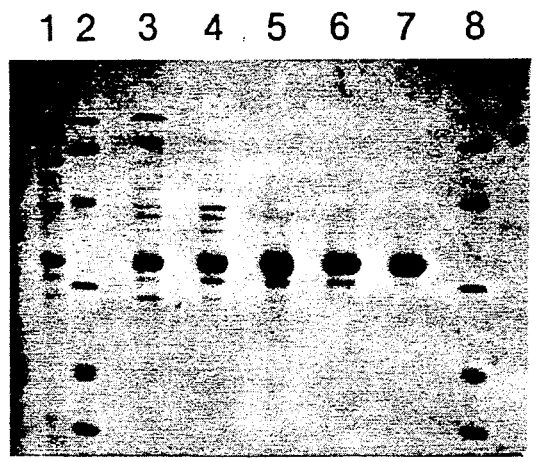
FIG. 4B shows the SDS-PAGE for each of the purification steps of recombinant synthase.

The purification of the enzyme throughout the process can be followed by SDS-PAGE. FIG. 4B of the drawings is a reproduction of the photograph of the gel following electrophoresis on samples of the enzyme at the various stages of the process. As shown by FIG. 4B, the lane corresponding to the single spot for the DAOC synthase is essentially free of other proteins.

The DAOC synthase obtained in active form from the above purification process for recombinant synthase was shown by a laser densitometric scan of the SDS-PAGE gel to be about 97% pure. Accordingly, the above-described process for purification of recombinant synthase is the preferred process of the invention.

The following examples are provided to further describe the invention and are not to be construed as limitations thereof.

Unless otherwise specified, DAOC synthase was assayed as follows: a reaction mixture of 1 ml contained 0.28 μmol of penicillin N, 0.3 μmol of α-ketoglutarate, 0.06 μmol of FeSO$_4$, 0.25 μmol of ascorbate, 1 μmol of dithiothreitol, and 0.0002 to 0.015 unit of the enzyme in 50 mM Tris-HCl buffer, pH 7.4. The enzymatic reaction was initiated by addition of penicillin N and was conducted for 15 min at 36° C. The synthase activity was determined by monitoring DAOC formation at 260 nm with HPLC as described by Dotzlaf, J. E., and Yeh, W. K (1987), *J. Bacteriol* 169, 1611–1618.

Example 1

Isolation and Purification of DAOC Synthase From *S. clavuligerus*

A strain of cephamycin-C producing *Streptomyces clavuligerus* ATCC 27064 was grown in 500 ml Erlenmeyer flasks using the conditions described by Whitney, J. G., et al., *Antimicrobial Agents and Chemotherapy*, Vol. 1, pp. 247–251 (1972). After culturing for 2 days the cells were harvested by centrifugation, washed with 15 mM Tris-HCl buffer, pH 7.5, in the presence of 10% ethanol and 1.0M KCl. The cells were then washed with the salt-free buffer and stored at −70° C. until needed.

The isolation and purification of DAOC synthase from the *S. clavuligerus* cells was carried out at a temperature between about 0° C. and about 4° C. All buffers were degassed thoroughly prior to use.

Fresh cells (wet weight 300 g) were suspended in 15 mM Tris-HCl, pH 7.5, in the presence of 10% ethanol (E buffer hereinafter) to a total volume of 600 ml. The cells were broken by sonication at 4° C. or below. During sonication additions of phenylmethylsulfonyl fluoride (PMSF), 2 mM, and deoxyribonuclease (1 μg/ml)/MgSO<(10 mM) were made to the suspension. Following sonication the broken cell suspension was centrifuged at 40,000 ×g for 30 min and the supernatant used as the crude cell extract.

The crude extract was applied by a DEAE-Trisacryl LS column (2.6×50 cm) previously equilibrated with E buffer. The column was washed with two bed volumes of E buffer and bound proteins were eluted with a linear gradient of KCl (0–0.35 M) in E buffer. DAOC synthase was eluted as a single activity peak well separated from DAOC hydroxylase activity (FIG. 1).

The peak fractions containing 60% of the total synthase activity were pooled and were concentrated to a volume of 5 ml by ultrafiltration with a B15 Minicon concentrator (Amicon). The concentrate was loaded onto an Ultragel A44 column (2.6×95 cm) previously equilibrated with E buffer and protein eluted with E buffer. A single activity peak was obtained.

The peak fractions containing 60% of the total synthase activity were pooled and applied to a Mono Q column (1×10 cm), Pharmacia, Inc., Piscataway, NJ, previously equilibrated with E buffer. Bound proteins were eluted with a linear gradient of KCl (0–0.5 M) in E buffer. A single activity peak was obtained. The fraction with the highest synthase activity was stored at −70° C. for further use. The main protein (i.e., with an $M_r$ of 34,000) from an aliquot (1.0 mg) of this fraction of the Mono Q column was further purified by electrophoretic elution from a 12% SDS-PAGE gel.

The SDS-PAGE analysis (FIG. 2) showed that the main protein accounted for about 50% of total protein from the fraction and after electrophoretic elution, was nearly homogenous. The gel-purified protein was, however, inactive as DAOC synthase. In FIG. 2, lanes 1 and 4 contain 2.5 μg of protein standards. Lanes 2 and 3, "Gel eluate", contain 5 μg of gel-eluted S. clavuligerus protein from purification of the native synthase.

The above-described three-step purification of the S. clavuligerus synthase is summarized in the following Table 3.

TABLE 3

Purification of DAOC Synthase from S. clavuligerus

| Step | Protein[1] (mg) | Activity[2] (U) | Sp Act[3] (U/mg) | Recovery (%) |
|---|---|---|---|---|
| Crude Extract | 7,166 | 25.77 | 0.0036 | 100 |
| DEAE-Trisacryl eluate | 268 | 6.50 | 0.0243 | 25 |
| Ultragel A44 eluate | 83 | 3.27 | 0.039 | 13 |
| Mono Q eluate | 7 | 1.16 | 0.166 | 5 |

[1]Protein content was determined by the method of Bradford, M. M. (1979), Anal. Biochem. 72, 248-254, using bovine serum albumin as the standard.
[2]One unit (U) of enzyme activity is defined as the amount of the synthase required to produce one μmol of DAOC per min from penicillin N in the assay procedure described hereinabove.
[3]Specific activity is the units (U) per mg of protein.

Example 2

Isolation and Purification of Recombinant DAOC Synthase

The following purification method was carried out at a temperature between about 0° C. and about 4° C. and all buffers were thoroughly degassed before use.

Escherichia coli K12 strain JM109 containing a copy of the DAOC synthase gene of S. clavuligerus was grown in 10-liter fermentors under the conditions described for shake flask cultures in copending application Ser. No. 192,273, filed May 9, 1988. About 6 hr after the temperature of the fermentation mixture shifted from 30° C. to 42° C., the E. coli cells were collected by centrifugation and were washed by the procedures used for the S. clavuligerus cells as described in Example 1.

The washed cells were suspended in 50 mM Tris-HCl, pH 7.5, buffer and disrupted in a Gaulin homogenizer. The granules enriched in DAOC synthase protein were isolated by differential centrifugation at 8,000 ×g for 1 min.

The granules were solubilized with 5 M urea in 15 mM Tris-HCl, pH 8.0, buffer in the presence of 5 mM dithiothreitol (DTT) and 10% glycerol (UDG buffer) and the mixture centrifuged at 40,000 ×g for 15 minutes to provide a granular extract (supernatant). The extract was applied to a DEAE-Sepharose (Pharmacia, Inc., Piscataway, NJ) column (1.6×25 cm) previously equilibrated with UDG buffer. The column was washed with two-bed volumes of the same buffer and bound proteins were eluted with a linear gradient of NaCl (0–0.3 M). The synthase was obtained as a single activity peak as shown in FIG. 3A.

The fractions containing 60% of the total enzyme activity were pooled and concentrated to a volume of 2 ml by ultrafiltration with a B15 Minicon concentrator (Amicon). The concentrate was applied to a Bio-Gel A0.5 m (Bio-Rad Laboratories, Richmond, CA) column (1.6×95 cm) previously equilibrated with UDG buffer. The bound protein was eluted with UDG buffer and a single activity peak was obtained as shown in FIG. 3B. The peak fractions containing 60% of the total chromatographic enzyme activity were pooled, supplemented with 0.1 mM penicillin N and loaded onto a Mono Q column (0.5×5 cm) previously equilibrated with the glycerol-free buffer (5 M urea, 15 mM Tris-HCl, pH 8.0, and DTT). The bound proteins were eluted with a linear gradient of NaCl (0–0.5 M) in the buffer used for equilibration of the column. Two activity peaks were obtained as shown in FIG. 3C.

The fractions containing 60% of the enzyme activity from the major peak were pooled, concentrated to a volume of 0.5 ml with a Centricon-30 (Amicon) and applied to a Superose (Pharmacia, Inc., Piscataway, NJ) column (1.6×85 cm) which was previously equilibrated with the glycerol-free buffer. Bound protein was eluted with the glycerol-free buffer supplemented with 0.1M KCl. Two partially separated activity peaks were obtained as shown in FIG. 3D.

The fractions containing 80% of the enzyme activity from the major peak were pooled. The pooled fractions were supplemented with 0.1 mM penicillin N and were loaded onto a second Mono Q column (0.5×5 cm) which had been equilibrated with the glycerol-free buffer, pH 7.0, (instead of pH 8.0 for UDG buffer), which was supplemented with 0.05 M KCl. The bound proteins were eluted with a linear gradient of KCl 0.05–0.2 M) in the equilibration buffer. The activity and protein elution patterns are shown in FIG. 4A. The three fractions with a synthase activity of at least 275 mU/ml were pooled.

The pooled eluate, when analyzed by SDS-PAGE, migrated as a major and a minor protein bond (FIG. 4B). A laser densitometric scan of the gel showed that the major protein was greater than 95% pure.

The above-described purification of the recombinant produced DAOC synthase is summarized in the following Table 4. The purified recombinant DAOC synthase is in an active form.

In FIG. 4B (SDS-PAGE of recombinantly produced DAOC synthase), lanes 2/8 contain 2.5 μg of protein standards; lane 1, 20 μg of granular extract, and lanes 3/7, 20 μg of DEAE-Sepharose eluate, Bio-Gel A 0.5m eluate, Mono Q I eluate, Superose 12 eluate and Mono Q II eluate, with reference to the following Table 4.

TABLE 4

Purification of DAOC Synthase From Recombinant *E. coli*

| Step | Protein (mg) | Activity (U) | Sp Act (U/mg) | Yield (%) |
|---|---|---|---|---|
| Granular extract | 464 | 25.69 | 0.0554 | 100 |
| DEAE-Sepharose eluate | 70.5 | 10.01 | 0.142 | 39 |
| Bio-Gel A0.5 m eluate | 35.2 | 6.89 | 0.196 | 27 |
| Mono Q I eluate | 10.3 | 2.32 | 0.225 | 9 |
| Superose 12 eluate | 4.4 | 1.03 | 0.235 | 4 |
| Mono Q II eluate | 1.2 | 0.52 | 0.432 | 2 |

The cloning procedure employed for the recombinant DAOC-producing strain of *E. coli* is carried out as follows.

A. Culture of *E. coli* K12 RR1ΔM15/pOW380

A lyophil of *E. coli* K12 RR1ΔM15/pOW380 can be obtained from the Northern Regional Research Laboratories (NRRL), Peoria, IL 61604, under the accession number NRRL B-18264 and used directly as the "culture" in the process described below.

One liter of TY broth (8 g tryptone, 5 g NaCl, and 5 g yeast extract per liter) containing 100 μg/mL ampicillin was inoculated with a culture of *E. coli* K12 RR1ΔM15/pOW380 and incubated with aeration at 37° C. overnight (15–18 hours). The resulting culture was used as a source of plasmid pOW380.

B. Isolation of Plasmid pOW380

The culture prepared in Example 1A was centrifuged at 5200 rpm for 10 minutes at 4° C. to pellet the cells. The resulting supernatant was discarded. The cell pellet was resuspended in 28 mL of a solution of 25% sucrose and 50 mM EDTA. About 1 mL of a solution of 20 mg/mL lysozyme in 50% glycerol and 0.25 M Tris-HCl, pH=8.0, and about 1.5 mL of 0.5 M EDTA, pH=8.0, were added to and mixed with the cell suspension. The resulting mixture was incubated on ice for 15 minutes. Three mL of lysing solution (prepared by mixing 3 mL of 10% Triton-X100; 75 mL of 0.25 M EDTA; pH=8.0; and 7 mL of water) were added to the lysozyme-treated cells with gentle mixing. The resulting solution was incubated on ice for another 15 minutes.

The cellular debris was removed from the solution by centrifugation at 17,000 rpm for about 45 minutes at 4° C. About 28.6 g of CsCl and ~1 mL of a 5 mg/mL ethidium bromide solution were added to the ~30 mL of supernatant. Then, the volume was adjusted to 40 mL with water and the solution decanted into an ultracentrifuge tube. The tube was sealed, and the solution was centrifuged at 49,500 rpm for ~18 hours. The resulting plasmid band, visualized with ultraviolet light, was isolated, extracted with salt-saturated isopropanol to remove the ethidium bromide, and dialysed against three changes of ~20 volumes of TE buffer (10 mM Tris-HCl, pH=7.5, and 1 mM EDTA). The dialysate was collected; then, two volumes of ethanol and 0.05 volumes of 3 M sodium acetate solution were added. The ethanol mixture was cooled to −20° C., and the plasmid DNA was pelleted by centrifugation at 10,000 rpm for 30 minutes at −10° C. The resulting pellet was resuspended in ~1 mL of TE buffer and then extracted with an equal volume of a phenol:chloroform mixture (1:1, v/v). The DNA in the aqueous phase was recovered by the addition of 0.1 volume of 3 M NaOAc and 2 volumes of ethanol, followed by incubation at −20° C. for ~30 minutes and centrifugation at 15,000 rpm for 20 minutes. The resulting DNA pellet was rinsed first with 70% ethanol and then with 100% ethanol and dried.

The ~1.5 mg of plasmid pOW380 DNA obtained by this procedure was suspended in 1.5 mL of 0.1 X TE buffer and stored at −20° C. A restriction site and function map of plasmid pOW380 is presented in FIG. 1 of the accompanying drawings.

Construction of Phage mOW380

Identical plasmid constructs can be achieved employing different methods and sources of gene sequences. Phage mOW380 was constructed by ligating the DAOCS gene-containing ~3 kb BamHI restriction fragment of cosmid pOW379 with BamHI-digested, replicative form (RF) M13 vector. The cosmid pOW379 clone originated from a *Streptomyces clavuligerus* genomic cosmid library and was identified by hybridization using not only the IPNS gene of *S. lipmanii* but also a "guessmer" DNA probe designed on the basis of the amino-terminal amino acid residue sequence of purified *S. clavuligerus* expandase and species codon-usage bias. The desired phage M13 clone can be identified using the "guessmer" probe in a plaque hybridization procedure or by restriction enzyme analysis. Because of the present invention, however, the construction of mOW380 is greatly simplified, primarily because plasmid pOW380 can be used as the source of the *S. clavuligerus* DAOCS gene. The M13-derived phage mOW380 was a useful intermediate in the site-specific mutagenesis carried out to create an NdeI restriction enzyme recognition site at the 5' end of the *S. clavuligerus* expandase coding sequence.

A. Isolation of the ~3 kb BamHI Restriction Fragment from Plasmid pOW380

Approximately 25 μg of the plasmid pOW380 DNA in 25 μl 0.1X TE buffer, as prepared in Example 1B, are added to and mixed with 40 μl of 10X BamHI buffer (1.0 M NaCl; 100 mM Tris-HCl, pH=b 7.5; and 100 mM MgCl₂), 335 μl of glass-distilled water, and 5 μl (~50 units) of restriction enzyme BamHI. Unless otherwise noted, restriction enzymes were obtained from New England Biolabs, 32 Tozer Road, Beverly, MA 01915. Unit definitions herein correspond to the particular manufacturer's unit definitions. The resulting reaction is incubated at 37° C. for 90 minutes. The reaction is then extracted with phenol and chloroform, and the BamHI-digested plasmid pOW380 DNA is precipitated with NaOAc and ethanol and then resuspended in 9 μl of H$_2$O. About 1 μl of loading buffer (25% v/v glycerol, 0.05% w/v bromphenol blue, and 0.05% xylene cyanol) is added to the solution of DNA, which is then electrophoresed on a 1% agarose gel until the desired ~3 kb BamHI restriction fragment is clearly separated from the other digestion products.

The electrophoresed DNA was visualized by staining the gel in a dilute solution (0.5 μg/ml) of ethidium bromide and exposing the stained gel to longwave UV light. After the fragments were located, a small slit was made in the gel in front of the ~3 kb fragment, and a piece of Schleicher and Schuell (Keene, NH 03431) DEAE membrane was placed in the slit. Upon further electrophoresis, the DNA non-covalently bound to the DEAE membrane. After the desired fragment was bound to the DEAE membrane, the membrane was removed and rinsed with low salt buffer (100 mM NaCl; 0.1 mM EDTA; and 20 mM Tris-HCl, pH=8). Next, the membrane was placed in a small tube and immersed in high salt buffer (1 M NaCl; 0.1 mM EDTA; and 20 mM Tris-HCl, pH=8) and then incubated at 65° C. for 10 minutes to remove the DNA from the DEAE paper. After the 65° C. incubation, the incubation buffer was collected, and the membrane was rinsed with high salt buffer. The rinse solution was pooled with the incubation buffer before collecting the desired DNA fragments.

The volume of the high salt-DNA solution was adjusted so that the NaCl concentration was 0.25 M, and then three volumes of cold, absolute ethanol were added to the solution. The resulting solution was mixed and placed on ice for 10–20 minutes. The solution was then centrifuged at 15,000 rpm for 15 minutes. After another precipitation to remove residual salt, the DNA pellet was rinsed with 70% ethanol, dried, resuspended in 20 μl of TE buffer, and constituted the desired restriction fragment. About 0.6 μg of the ~3 kb fragment was obtained.

B. Preparation of BamHI-Digested Vector M13mp19 RF DNA and Construction of Phage mOW380

About 2.5 μg of M13mp19 RF DNA (available from New England Biolabs (NEB)) were digested in 100 μl of BamHI buffer with 1 μl (~20 units) of restriction enzyme BamHI for 90 minutes at 37° C. The reaction mixture was extracted with phenol:chloroform and the DNA, in the aqueous phase, concentrated by ethanol precipitation. The DNA pellet was resuspended in 20 μl of 0.1X TE buffer and constituted ~2 μg of the desired BamHI-digested M13mp19 vector. The vector DNA obtained was stored at −20° C.

Two μl of the ~3 kb BamHI restriction fragment of plasmid pOW380 and 1 μl of BamHI-digested vector M13mp19 are ligated in a 20 μl reaction containing the DNA fragments, 2 μl of 10X ligase buffer (0.5 M Tris-HCl, pH 7.5, and 100 mM MgCl$_2$), 2 μl of 5 mM ATP, 1 μl of Weiss unit) of T4 DNA ligase (NEB). The reaction is incubated ~18 hours at 15° C. The ligated DNA constitutes the desired phage mOW380 along with other ligation products.

Competent *E. coli* K12 JM109 ("Epicurean Coli ™") were purchased from Stratagene (3770 Tansy Street, San Diego, CA 92121) and transformed with a ligation reaction mixture constituting phage mOW380 in substantial accordance with the manufacturer's directions, except that the DNA was in a volume of 20 μl and no dilution into medium or expression time was necessary. Post-transformation, the cells were distributed in ~1, 10, 20, 40 and 50 μl samples to 13×100 mm sterile glass tubes containing 0.25 mL/tube *E. coli* K12 JM109 in logarithmic growth phase. To these tubes were added 3 mL of top agar (L broth with 0.8% agar kept molten at 45° C). The cell-top agar mixture was then plated on L-agar plates containing 40 μg/mL 5-bromo-4-chloro-3-indolyl-β-D-galactoside (X-gal) and 0.1 M isopropylthio-β-galactoside (IPTG), and the plates were incubated at 37° C. overnight. (For more detailed descriptions and explanations of M13 procedures, see *M13 Cloning/Dideoxy Sequencing Instruction Manual*, Bethesda Research Laboratories (BRL), Life Technologies, Inc., Gaithersburg, MD 20877.) Transformants are identified by insertional inactivation of β-galactosidase activity (colorless plaque phenotype) and restriction enzyme analysis of replicative form (RF) DNA. For screening purposes, clear plaques are plugged from the plate overlay with a Pasteur pipette into 3 mL per plaque of early logarithmic growth phase *E. coli* K12 JM109. Cultures are incubated from 6 to 18 hours at 37° C. with aeration.

Following this incubation, 1.5 mL of each culture are pelleted in separate 1.5 mL Eppendorf tubes. The supernatants are decanted into fresh tubes and stored at 4° C. to serve as a source of phage inoculum. Replicative form DNA is prepared from the cell pellets in substantial accordance with the teaching of the alkaline plasmid preparation procedure of Birnboim and Doly, 1979, *Nuc. Acid Res.* 7(6): 1513–1523, with the following exceptions. The procedure is scaled up such that 1.5X volumes of Solutions I, II, and III are used, and the cleared lysate is extracted once with an equal volume of CHCl$_3$. The DNA is then precipitated by the addition of 0.4 volumes of isopropanol and incubation at room temperature for 20 minutes. The DNA is collected by centrifugation and then precipitated with ethanol out of 0.3 M NaOAc. The analysis of the restriction pattern of the RF DNA is facilitated by the existence of an assymetric ScaI restriction enzyme recognition site that is not only diagnostic for the presence of the desired insert but also can be used to orient the insert sequence relative to the multiple-cloning site (MCS) of the M13 vector. By this method, *E. coli* K12 JM109/mOW380 cells were identified; these cells were then used as a source of phage mOW380 for the site-specific mutagenesis, as described below.

C. Preparation of Single-Stranded Phage mOW380 DNA and Site-Specific Mutagenesis to Construct Phage mOW381

A 10 mL culture of early logarithmic growth phase *E coli* K12 JM109 was inoculated with ~200 μl of phage stock (prepared in Example 2B) and incubated ~18 hours at 37° C. with aeration. The culture was centrifuged and the resulting supernatant transferred to a new tube and recentrifuged. The supernatant was again decanted to a fresh tube. One mL of a solution of 25% polyethylene glycol (molecular weight ≈3,350) in 3 M NaCl was added to the supernatant, which was then incubated for 15 minutes at room temperature. The resulting mixture was centrifuged for 30 minutes at 10,000 rpm. The pellet obtained by the centrifugation contained the single-stranded phage mOW380 and was resuspended in 400 μl of TE buffer. The solution was extracted first with CHCl$_3$ and then with TE-saturated phenol. The phenol was allowed to stay in contact with the aqueous phase for 15 minutes. The solution was then extracted twice with a mixture of TE-saturated phenol:CHCl₃ (1:1, v/v), and twice with CHCl₃ alone. The DNA was then precipitated out of 0.3 M NaOAc, collected by centrifugation, and the resulting pellet resuspended in 100 µl of 0.1X TE buffer. This solution constituted ~5 µg of single-stranded phage mOW380 DNA.

D. Mutagenesis

The single-stranded DNA fragments used in the mutagenesis (and subsequent hybridizations to detect desired phages) were synthesized on an automated DNA synthesizer, with the exception of the M13 universal primer (a 15-mer), which was purchased from BRL. The mutagenesis fragments were designated as follows:

(1) STNDE-A, a single-stranded DNA 41 nucleotides in length that is homologous to the DAOCS coding sequence in phage mOW380 except for three bases, the mismatch (underlined) of which will create a restriction enzyme NdeI recognition sequence at about position 1 of the DAOCS coding sequence, with the DNA sequence:

```
                                NdeI
5'-GTGGGCACCGTCGTGTCCATATGCTCTCACTGATCCTCTCG-3'
```

(2) STNDE-B, a single-stranded DNA 17 nucleotides in length that is merely a subfragment of STNDE-A, with the DNA sequence:

```
            NdeI
5'-TGTCCATATGCTCTCAC-3'
```

The 5' ends of about 100 pmols of STNDE-A were phosphorylated (kinased) in a reaction mixture containing single-stranded DNA at a concentration of 1 pmol/µl, 10 l of 10X ligase buffer, 1000 pmols adenosine triphosphate (ATP), 10 µl of 0.1 M DTT, 65 µl of glass-distilled water, and 1 µl (10 Richardson units) of T4 polynucleotide kinase (Boehringer-Mannheim Biochemicals, (BMB) 7941 Castleway Drive, P.O. Box 50816, Indianapolis, Indiana 46250). The reaction mixture was incubated at 37° C. for 30 minutes, at which time an additional 1 µl of enzyme was added. The reaction mixture was then incubated for another 30 minutes at 37° C. and then quenched by incubation at 68° C. for 5 minutes. The 5' ends of about 40 pmols pf M13 universal primer were kinased in an analogous 40 µl of reaction mixture containing the same amount of enzyme.

The single-stranded phage mOW380 DNA was mutagenized in substantial accordance with the teaching of Adelman et al., 1983, DNA 2(3): 183-193 as described below. The annealing reaction was carried out by adding ~500 nanograms (in 15 µl of 0.1X TE buffer) of singlestranded phage mOW380 DNA to 8 µl of 10X annealing buffer (100 mM Tris-HCl, pH=7.5; 1 mM EDTA; and 500 mM NaCl), 4 µl (4 pmols) of kinased STNDE-A, 4 µl (4 pmols) of kinased M13 universal sequencing primer, and 50 µl of water, incubating the mixture at 80° C. for 2 minutes, then at 55° C. for 5 minutes, and finally at room temperature for 5 minutes.

The extension reaction was carried out by adding 120 µl of the following mixture to the solution of annealed DNA: 20 µl 10X Klenow-ligase buffer (100 mM Tris-HCl, pH=7.5; 1 mM EDTA; and 500 mM NaCl), 20 µl of 0.1 M DTT; 20 µl of a solution 6.25 mM in each of dGTP, dATP, TTP, and dCTP; 20 µl of 5 mM ATP; 120 µl of water; and 2.5 µl (12.5 units) of Klenow enzyme (BMB). The extension reaction mixture was incubated at room temperature for 1 hour, then at 37° C. for 4 hours, and finally at 14° C. for ~18 hours.

The extension reaction mixture was extracted once with CHCl₃ and the DNA precipitated with ethanol and NaOAc and collected by centrifugation. The DNA pellet was resuspended in 400 µl 1X S1 buffer (0.3 M NaCl and 3 mM ZnOAc). Half the DNA solution was held in reserve at −20° C; half was aliquoted to five 1.5 mL tubes. To four of these tubes was added 1 µl of S1 nuclease (BMB) that had been diluted to 200 30-minute units per µl. The reactions were incubated at room temperature for 5, 10, 15, and 20 minutes, respectively. The reactions were stopped by first adding 5–10 µg of tRNA to the reaction mixture to serve as carrier, then extracting with a TE-saturated phenol-CHCl₃ mixture (1:1, v/v). The sample that was not treated with S1 (the negative control) was also extracted. The DNA in the aqueous phase was concentrated by ethanol precipitation and collected by centrifugation. The DNA pellets were each resuspended in 20 µl water.

Ten µl of each of the resulting S1-treated DNA solutions were used to transform E. coli K12 JM109 in substantial accordance with the procedure described in Example 2B, except that the plates did not contain either X-Gal or IPTG. Desired mutants were identified by hybridization of radiolabelled oligonucleotide STNDE-B with phage DNA blotted onto nitrocellulose filters as described below.

After plaque formation, the plates were incubated at 4° C. for ~1 hour to harden the top agar. with a Quanta III ® intensifying screen (DuPont, Instrument Products, Biomedical Division, Newtown, CN 06470). Desired mutants, those containing sequences complementary to the sequence of STNDE-B, exposed the film due to binding of the radiolabelled oligomer by the phage DNA bound to the filter. The identity of a correct mutant, designated phage mOW381, was confirmed by restriction analysis of its RF DNA, which was prepared in substantial accordance with the procedure described in Example 2B.

E. Final Construction of Plasmid pOW381

Although the RF DNA of phage mOW381 contains the DAOCS coding sequence on the NdeI-BamHI restriction fragment utilized in the construction of the E. coli expression plasmid pOW382, it is sometimes difficult to accumulate the RF of mOW381 in sufficient quantity for fragment isolation. To facilitate the construction of the E. coli expression plasmid pOW382, the intermediate plasmid pOW381 was constructed.

Replicative form DNA from phage mOW381-infected E. coli K12 JM109 was isolated in substantial accordance with the procedure described in Example 2B. About 10 µg of the RF DNA of phage mOW381 DNA were digested with restriction enzyme BamHI (~10 units) in a reaction containing the DNA in 1X BamHI buffer. After incubation for ~90 minutes at 37° C., the reaction mixture was subjected to agarose gel electrophoresis, and the ~3 kb BamHI fragment was isolated in substantial accordance with Example 2A.

Nitrocellulose filters were placed on top of the lawn of each of two plates, containing ~50-200 plaques, from each of the negative control, the 10 minute S1-treated series, and the 20 minute S1-treated series. Contact between the filter and the surface of the lawn was maintained for ~1 minute, at which time the nitrocellulose filter was treated, by using saturated 3 MMChr filter papers (Whatman LabSales, Inc., P.O. Box 1359, Hillsboro, Oregon 97123-1359), with 0.1 N NaOH-1.5 M NaCl for ~5 minutes, then 0.5 M Tris-HCl(pH=7.0)-3 M NaCl for ~5 minutes. The nitrocellulose filters were air-dried and then baked in vacuo at 80° C. for 30 minutes.

The nitrocellulose filters were prehybridized for ~5 minutes at room temperature in a solution of 6X SSC (20X SSC is 3 M NaCl and 0.3 M Na citrate), 10X Denhardt's solution (0.2 g of polyvinylpyrollidone), 0.2 g of bovine serum albumin, and 0.2 g of Ficoll per 100 mL of water), 0.1% NaPPi, 0.1% SDS, and 10 μg/mL of denatured E. coli chromosomal DNA. The filters were then hybridized in a solution of 6X SSC., 10X Denhardt's solution, 0.1% NaPPi, and 1 pmol/5 mL of $^{32}$P-STNDE-B. The $^{32}$P-STNDE-B was prepared by phosphorylating the 5' ends of 100 pmols of STNDE-B in substantial accordance with the procedure described earlier in this example, except that ~70 pmol of γ-$^{32}$P-ATP (New England Nuclear (NEN), 549 Albany Street, Boston, MA, 02118, Catalog # NEG-002A) were used instead of non-radioactive ATP. After hybridization, the filters were rinsed twice for 5 minutes per wash in excess 6X SSC at room temperature, then at 52° C. in excess 6X SSC for 20 minutes per wash. The filters were air-dried and autoradiographed for 2 hours at −70° C.

BamHI-digested plasmid pUC8 DNA (plasmid pUC8 DNA is available from BRL) was prepared in substantial accordance with the procedure described in Example 2B. Five μl (μ1 μg) of the ~3 kb BamHI fragment DNA isolated from phage mOW381 and 1 μl (~100 ng) of BamHI-digested plasmid pUC8 DNA were ligated in substantial accordance with the procedure described in Example 2B. The ligated DNA constituted the desired plasmid pOW381 along with other ligation products.

Plasmid pOW381 has a restriction site map identical to that of plasmid pOW380, except for the presence of an additional NdeI restriction enzyme recognition sequence located at about the first codon of the DAOCS coding sequence.

The ligation reaction constituting the desired plasmid pOW381 was transformed into competent E. coli K12 RR1ΔM15 (NRRL B-15440). Aliquots of the transtaining ampicillin (100 μg/mL), X-gal (40 μg/mL), and IPTG (0.1 M). The plates were incubated at 37° C. for ~18 hours. Ampicillin-resistant transformants with a white colony color (due to insertional inactivation of the α-fragment of β-galactosidase encoded in plasmid pUC8) were further screened by restriction enzyme analysis of their plasmid DNA to identify the desired plasmid pOW381 transformants. Plasmid DNA was prepared from 3 mL cultures in substantial accordance with the Birnboim and Doly procedure described above for preparing RF DNA from phage M13-infected E. coli K12 JM109 cell pellets. Plasmid pOW381 DNA from one transformant was prepared in substantial accordance with the procedure described in Example 1 for use in subsequent constructions.

Construction of Plasmid pOW382

Plasmid pOW382 can be constructed by ligating together the ~2.4 kb NdeI-BamHI restriction fragment from plasmid pOW381 that contains the Streptomyces clavuligerus expandase (DAOCS) coding sequence and an ~5.8 kb NdeI-BamHI restriction fragment from plasmid pCZR336. The ~5.8 kb NdeI-BamHI fragment from pCZR336 contains DNA sequences coding for the λpL promoter, a translation activating sequence, the cI857 repressor, a plasmid origin of replication, and a tetracycline resistance-conferring gene. Plasmid pCZR366 also contains a coding sequence for human growth hormone. The DNA sequences contained in the ~5.8 kb NdeI-BamHI fragment of plasmid pCZR336 can be constructed as described in Part A of this Example. A restriction site and function map of plasmid pCZR336 is presented in FIG. 2 of the accompanying drawings.

A. Construction of the ~5.8 kb NdeI-BamHI Restriction Fragment of Plasmid pCZR336

Most of the DNA in the ~5.8 kb NdeI-BamI restriction fragment of plasmid pCZR336 can be isolated from plasmid pCER111 on an ~5.75 kb XbaI-BamHI restriction fragment. A restriction site and function map of plasmid pCZR111 is presented in FIG. 4 of the accompanying drawings. Plasmid pCZR111 can be obtained from E. coli K12 RV308/pCZR111, available from the NRRL under accession number NRRL B-18249. Plasmid pCZR111 confers resistance to 10 μg/ml tetracycline and lacks a ClaI restriction site.

Plasmid pCZR111 is also digested with XbaI and BamHI enzymes, and the large XbaI-BamHI fragment is purified from agarose. This XbaI-BamHI restriction fragment of plasmid pCZR111 is ligated together with a double stranded XbaI-NdeI restriction fragment synthesized by the phosphotriester method to yield the ~5.8 kb NdeI-BamHI restriction fragment of plasmid pCZR336 (FIG. 2). The double stranded DNA fragment has the following sequence:

```
5'-CTAGAGGGTATTAATAATGTATATTGATTTTAATAAGGAGGAATAATCA-3'
   ||||||||||||||||||||||||||||||||||||||||||||||||
3'-TCCCATAATTATTACATATAACTAAAATTATTCCTCCTTATTAGTAT-5'
```

B. Isolation of ~2.4 kb NdeI-BamHI fragment of Plasmid pOW381

Approximately 25 μg (in 25 μl of 0.1X TE buffer) of plasmid pOW381 DNA were added to and mixed with 4 μl of 10X NdeI buffer (100 mM Tris-HCl, pH 7.8; 70 mM MgClz; and 1.5 M NaCl) 6 μl of H$_2$O, 3 μl of restriction enzyme NdeI, and 3 μl of restriction enzyme BamHI. The resulting reaction mixture is incubated at 37° C. for 2 hours and subsequently subjected to agarose gel electrophoresis. The ~2.4 kb NdeI-BamHI fragment is isolated from the agarose gel and prepared for ligation.

C. Final Construction of Plasmid pOW382 and E. coli K12 JM109/pOW382

About 1 μl (~0.5 μg) of the ~5.8 kb NdeI-BamHI-restriction fragment of plasmid pCZR336 DNA and 4 μl (~0.1 μg) of the isolated ~2.4 kb NdeI-BamHI restriction fragment from pOW381 were ligated in substantial accordance with the procedure described in Example 2. The ligated DNA constitutes the desired plasmid pOW382. A restriction site and function map of plasmid pOW382 is presented in FIG. 3 of the accompanying drawings. The ligation reaction was transformed into competent E. coli K12 JM109 cells (Stratagene) in accordance with the manufacturer's directions. The transformation mix was plated onto TY agar plates containing tetracycline (10 μg/mL) and the plates incubated at 25°-30° C. to prevent transcription from the lambda pL promoter. Desired transformants were identified by their tetracycline-resistant phenotype and by restriction enzyme analysis of their plasmid DNA.

Assay of E. coli-produced DAOCS Activity

A. Culture of E. coli K12 JM109/pOW382 for Expression of DAOCS Activity

An E. coli K12 JM109/pOW382 transformant was grown at 30° C. overnight in 500 ml of L broth (containing 10 μg/ml of tetracycline) in a gyrotory incubator (250 rpm). The cells were diluted 100 fold by adding 10 ml of the overnight culture to 990 ml of fresh medium containing 10 μg/ml tetracycline in a 2.8 L flask and incubated a further hour at 30° C. under the same growth conditions. The temperature of the gyrotory incubator shaker was then raised to 42° C. and incubation continued for an additional 6.5 hours. The cI857 temperature-sensitive repressor of the lambda pL promoter, positioned to drive expression of the DAOCS coding sequence on plasmid pOW382, is inactivated at 42° C., so at 42° C. expression of DAOCS occurs in the host cells. After induction, the cells were harvested by centrifugation and used as a preferred source of E. coli-produced DAOCS activity.

We claim:

1. A process for preparing deacetylcephalosporin C which comprises contacting in the presence of oxygen, 3-exomethylenecephalosporin C of the formula

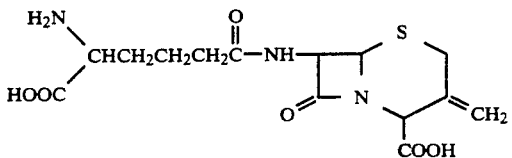

at a temperature between about 30° C. and about 40° C. in an aqueous medium containing ferrous ion and α-ketoglutarate at a pH between about 6.8 and about 7.6 with Streptomyces clavuligerus derived deacetoxycephalosporin C synthase.

2. The process of claim 1 wherein the pH is between about 7.0 and about 7.4.

3. The process of claim 1 wherein the temperature is about 36° C.

4. The process of claim 1 wherein the ferrous ion is present at a concentration between about 20 μM and about 100 μM.

5. The process of claim 1 wherein the α-ketoglutarate is present at a concentration between about 20 μM and about 300 μM.

* * * * *

UNITED STATES PATENT AND TRADEMARK OFFICE
CERTIFICATE OF CORRECTION

PATENT NO. : 5,082,772

DATED : January 21, 1992

INVENTOR(S) : Dotzlaf, et al.

It is certified that error appears in the above-identified patent and that said Letters Patent is hereby corrected as shown below:

Title Page, under [56] OTHER PUBLICATIONS, "*Attorney, Agent, or Firm* - William B. Scasnlon; Leroy Whitaker" should read; --*Attorney, Agent, or Firm* - William B. Scanlon; Leroy Whitaker--.

Column 14, line 68, "CHCla" should read, --$CHCl_3$--.

Signed and Sealed this

Eighth Day of September, 1998

Attest:

BRUCE LEHMAN

*Attesting Officer*   Commissioner of Patents and Trademarks